United States Patent
Jensen

(10) Patent No.: US 12,207,635 B2
(45) Date of Patent: Jan. 28, 2025

(54) ARTICLE, METHOD FOR PRODUCING A KNOTTING DEVICE FOR THE ARTICLE, METHOD FOR PRODUCING AN ARTICLE AND METHOD FOR FORMING AND TIGHTENING A KNOT

(71) Applicant: CLOUZ GMBH, Berlin (DE)

(72) Inventor: Anne-Mette Jensen, Berlin (DE)

(73) Assignee: CLOUZ GMBH, Berlin (DE)

( * ) Notice: Subject to any disclaimer, the term of this patent is extended or adjusted under 35 U.S.C. 154(b) by 0 days.

(21) Appl. No.: 18/026,849

(22) PCT Filed: Sep. 10, 2021

(86) PCT No.: PCT/EP2021/074990
§ 371 (c)(1),
(2) Date: Mar. 17, 2023

(87) PCT Pub. No.: WO2022/058250
PCT Pub. Date: Mar. 24, 2022

(65) Prior Publication Data
US 2023/0329699 A1    Oct. 19, 2023

(30) Foreign Application Priority Data
Sep. 21, 2020 (EP) .................... 20197218

(51) Int. Cl.
*A01K 91/04* (2006.01)
*B65B 13/26* (2006.01)
*B65H 69/04* (2006.01)

(52) U.S. Cl.
CPC ............ *A01K 91/04* (2013.01); *B65B 13/265* (2013.01); *B65H 69/04* (2013.01)

(58) Field of Classification Search
CPC ........ A61B 17/06114; A61B 17/06061; A61B 2017/0479; A61B 2017/0496; B65H 69/04
See application file for complete search history.

(56) References Cited

U.S. PATENT DOCUMENTS 1,171,194 A * 2/1916 Knowlton ............... B65D 85/04
                                                                 206/388
3,869,044 A 3/1975 Olsson et al.
(Continued)

FOREIGN PATENT DOCUMENTS

DE    2 044 486 A1    4/1971
FR    2 331 638 A1    6/1977
(Continued)

OTHER PUBLICATIONS

International Search Report & Written Opinion for PCT/EP2021/074990 mailed on Nov. 30, 2021.

Primary Examiner — Bao-Thieu L Nguyen
(74) Attorney, Agent, or Firm — Schmeiser, Olsen & Watts LLP

(57) ABSTRACT

An article and method for supporting a user in providing and tightening a knot is provided. The article includes a knotting device and thread, including a base section, a thread storage section, and a knot support element including at least one flap folded into a frustoconical shape, being hollow and open on a base end of the frustoconical shape and on a tip end of the frustoconical shape the thread includes a first and a second end opposite the first end along the length of the thread. The first end of the thread is arranged in the thread storage section and the second end of the thread forms a plurality of windings of a non-tightened knot, one of which is arranged on and around an outer surface of the frustoconical shape of the knot support element, the knot support (Continued)

element thereby supporting and holding open the non-tightened knot.

15 Claims, 9 Drawing Sheets

(56) References Cited

U.S. PATENT DOCUMENTS

| | | | | |
|---|---|---|---|---|
| 3,876,068 | A * | 4/1975 | Sonnino | A61B 17/06138 242/159 |
| 4,884,681 | A * | 12/1989 | Roshdy | A61B 17/06138 206/63.3 |
| 4,887,710 | A * | 12/1989 | Roshdy | A61B 17/06138 206/63.3 |
| 5,127,518 | A * | 7/1992 | Holzwarth | A61B 17/06138 53/461 |
| 5,174,087 | A * | 12/1992 | Bruno | A61B 17/0401 606/228 |
| 5,566,821 | A * | 10/1996 | Brown | A61B 17/06138 206/388 |
| 5,746,311 | A * | 5/1998 | Brown | A61B 17/06138 53/477 |
| 11,857,408 | B2 * | 1/2024 | Marks | A61F 2/0095 |
| 2018/0206841 | A1 | 7/2018 | Oldham et al. | |

FOREIGN PATENT DOCUMENTS

| | | |
|---|---|---|
| WO | 96/02194 A1 | 2/1996 |
| WO | 2016/005118 A1 | 1/2016 |
| WO | 2019/106189 A1 | 6/2019 |

* cited by examiner

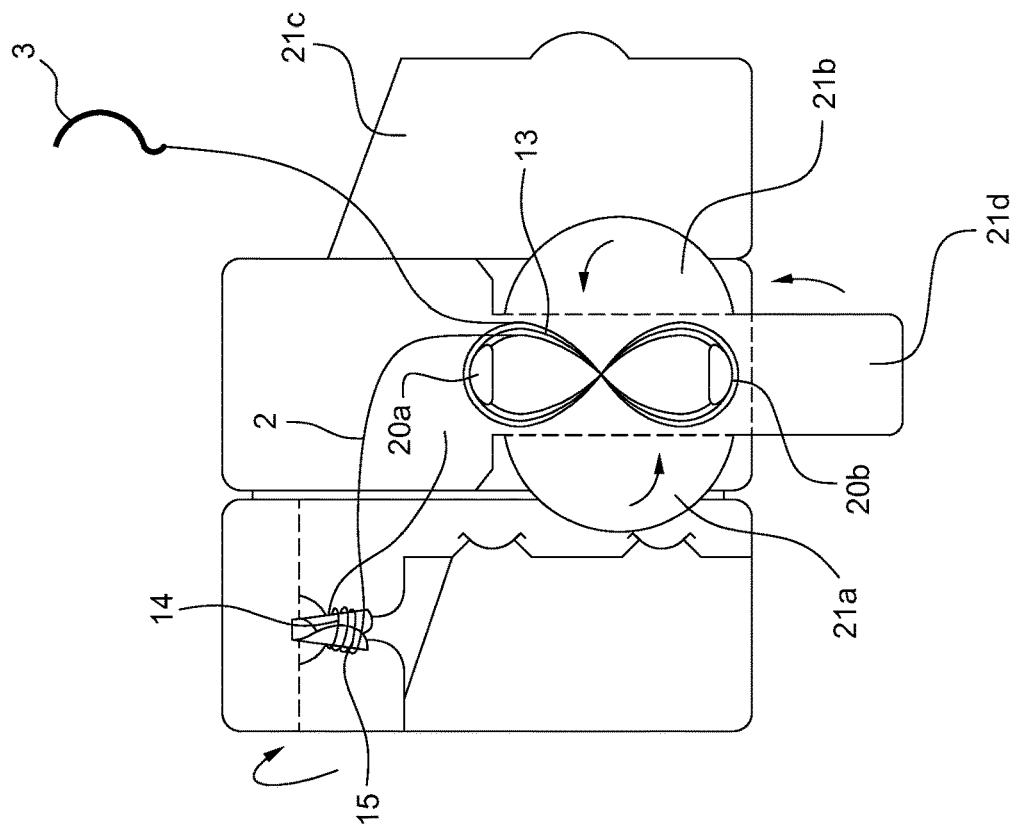
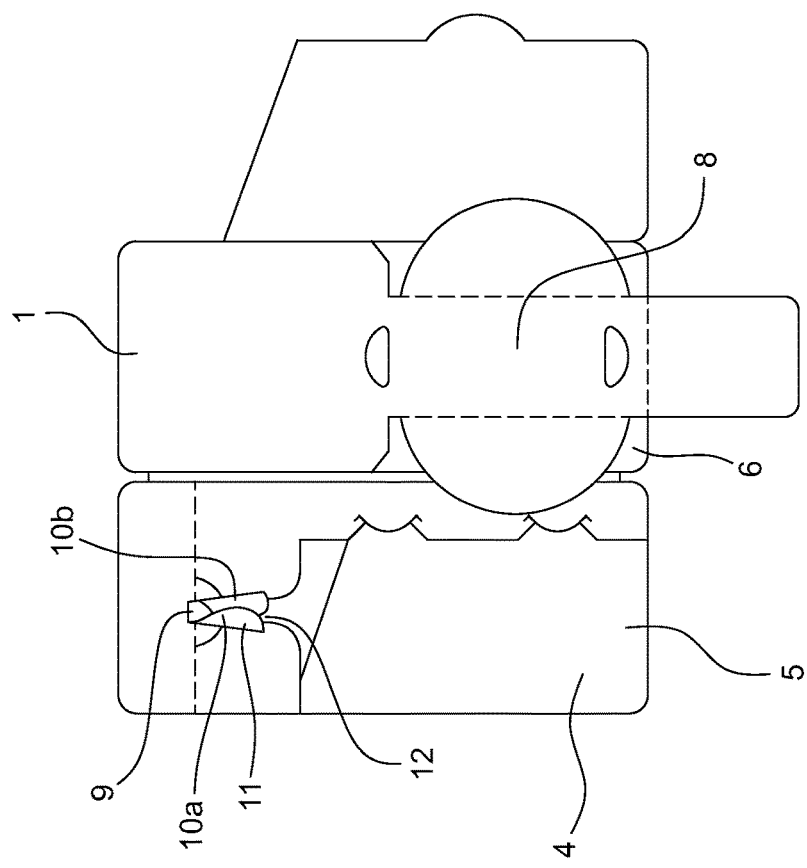
Fig. 4B
Fig. 4A

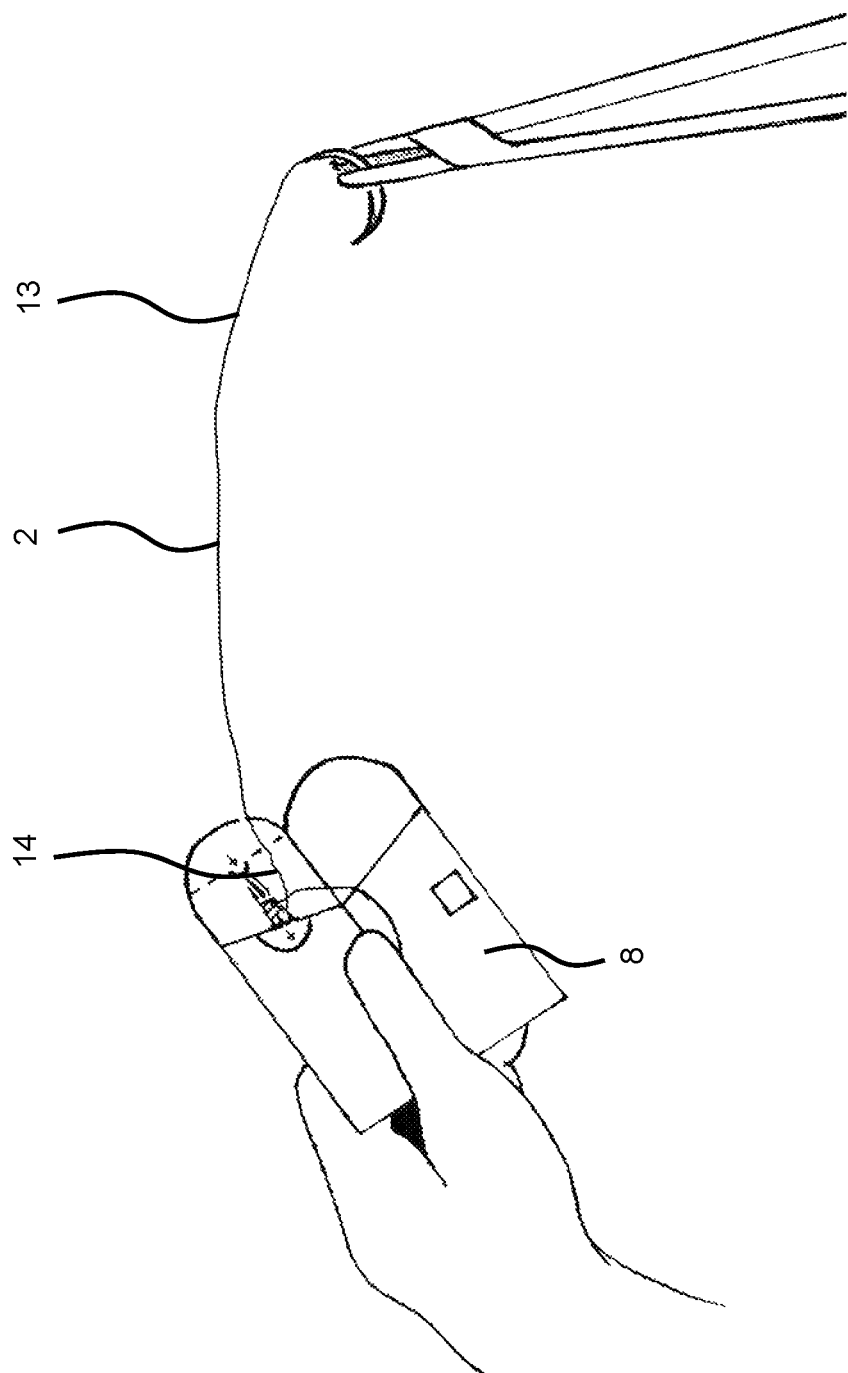

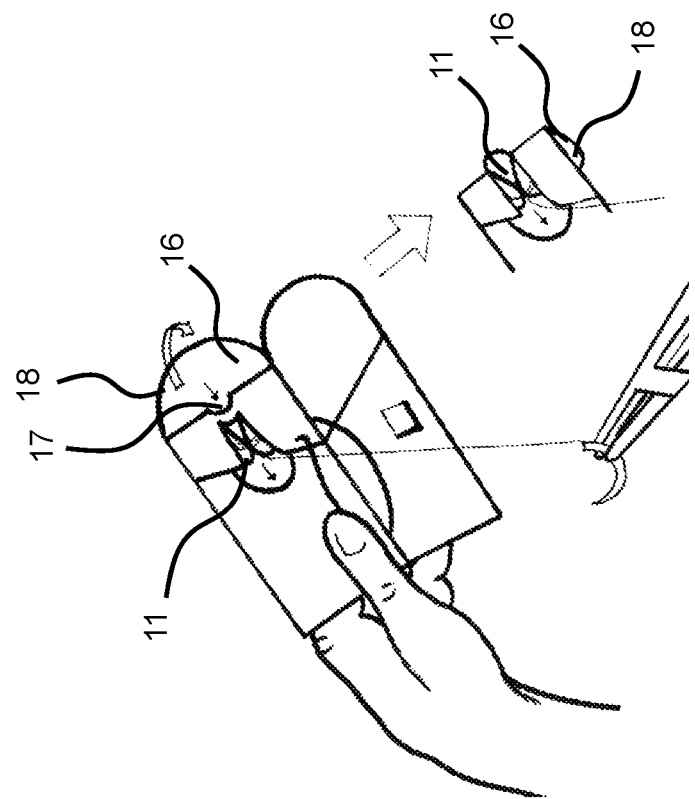
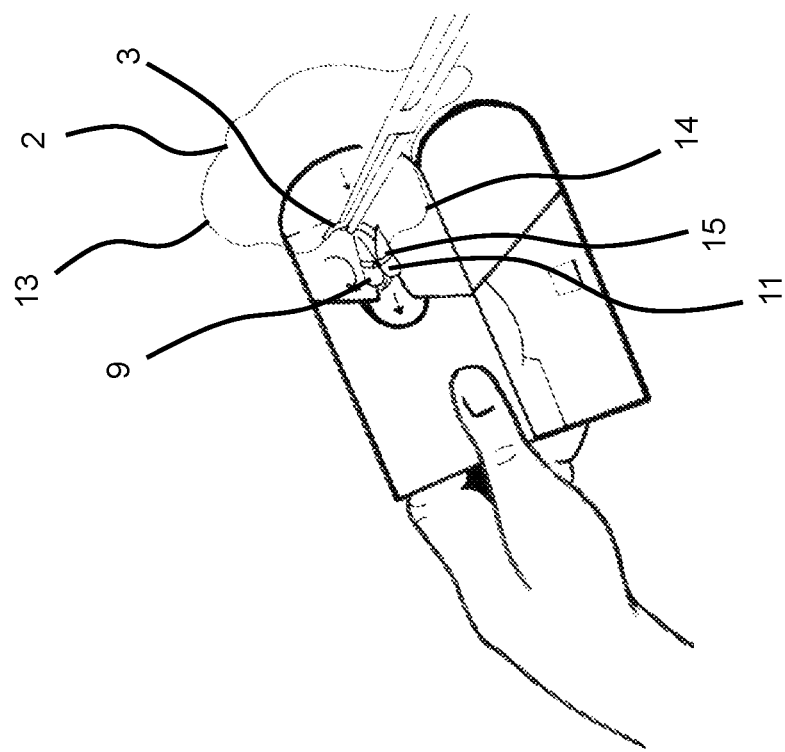
Fig. 5C
Fig. 5D

ARTICLE, METHOD FOR PRODUCING A KNOTTING DEVICE FOR THE ARTICLE, METHOD FOR PRODUCING AN ARTICLE AND METHOD FOR FORMING AND TIGHTENING A KNOT

CROSS-REFERENCE TO RELATED APPLICATIONS

This application claims priority to PCT Application No. PCT/EP2021/074990, having a filing date of Sep. 10, 2021, which is based on EP Application No. 20197218.9, having a filing date of Sep. 21, 2020, the entire contents both of which are hereby incorporated by reference.

FIELD OF TECHNOLOGY

The following invention refers to an article, a method for producing a knotting device for the article, a method for producing an article as well as a method for forming and tightening a knot.

BACKGROUND

Tying knots is an intricate task and tying knots that fulfil certain requirements, in particular with regard to strength and durability, may be cumbersome or impossible in certain use situations. For example, in model building, it may be necessary to place an intricate knot at a minuscule detail of the model to be built, which may in addition be hard to reach, such as in the case of a ship in a bottle.

In the medical field, tying knots in restrictive access or minimally invasive surgery, for example Laparo-Endoscopic Single-Site Surgery (LESS) is technically difficult and time-consuming. At the same time, minimally invasive surgery is widely accepted as having great advantages over open surgery, both in terms of patient outcomes and cost of care. Among patient benefits are less pain and less scarring, reduced anesthesia time, shorter recovery and hospital stay, and a quicker return to normal activity while economic benefits include lower post-operative complication rates, shorter hospitalization and reduced cumulative treatment costs.

Minimally invasive procedures are conducted through tiny incisions in the body, using long thin instruments to perform the operation. Another incision may be used for the camera, which gives the surgeon a restricted, usually two-dimensional view of the workspace. Space and movements are extremely restricted, which makes tying surgical knots to fixate tissue, organs or closing an internal wound, a complex technical challenge. It is time consuming, requires extensive practice, and it is difficult to ensure a consistently reliable result. Knots not tied properly may loosen after the operation, leading to serious complications and/or repeat surgery.

Patient demand for minimally invasive surgical procedures is on an increase, but adoption is hampered by procedure costs and lack of technical skills. The suturing and especially the tying of knots in minimally invasive surgery are a serious technical challenge. For these reasons, some surgeons may opt for open surgery methods instead.

Suturing assisting devices and alternative surgical closure solutions in use today include for example glue, strips, staplers, and mechanical suturing devices. Some devices are adapted for specific use cases, such as barbed sutures for soft tissue approximation or pre-made lasso knots for laparoscopic ligation, while other solutions are mechanically complex devices that are costly in use.

Suture assisting devices and laparoscopic closure devices are known, for example, from the documents WO 96/02194 A1 and US 2018/0206841 A1. Such devices are mechanically complex and relatively costly per patient use.

Other comparative products include so-called lasso knots, which provide no locking mechanism and necessitate security knots to be tied manually, and barbed sutures which provide low tension fixation without requiring knotting but offer no strong fixation.

The conventional suture kit consisting of a needle attached to a suture is the least costly and complex, and still the most widely used solution today for surgical closure. Examples of such suture kits are known from the documents DE 2 044 486 A1, U.S. Pat. Nos. 5,127,518 A, 5,174,087 A and U.S. Pat. No. 5,566,821 A.

The document U.S. Pat. No. 3,869,044 discloses a device in which very fine surgical sutures having needles thereon are wound from the needled end on a printed reel-label which is cut from a single piece of label stock in such fashion that the very fine sutures are wound over folded edges rather than cut edges to protect them from being frayed by the cut edges of the label stock. The suture on the reel-label is stored in a protective envelope, for example in a strippable outer envelope.

In the document FR 2 331 638 A1, a holder for a needle of thread, such as a surgical thread, is described. The holder consists of a kind of envelope with a flap. It is formed by thin parallel plates attached in part along their edges by side walls having an outwardly facing concave section for winding on the thread. A narrow slit is provided in one plate for the point of the needle and there are open grooves for trapping the ends of the thread. A flap covers the needle.

The document U.S. Pat. No. 3,876,068 relates to a suture reel-label package in which surgical sutures, including ligatures, are wound from a needled or free end on a printed reel-label. The reel-label is made from sealed together thicknesses of stiff inert sterilizable label stock, with means, such as an aperture or grommet, to act as a notable axis to permit holding between a finger and thumb for unwinding. A needle, if attached, is held in a pocket between the thicknesses with the armed portions of the needle protected. The friction between the thicknesses and the suture permits retention of the suture during storage and unwinding from either end. The suture reel assembly is stored in a sterile envelope which may be completely dry.

In the document WO 2019/106189 A1, an insert holding device and a suture holding device are disclosed which are used for connecting a suture to an insert for insertion into a bone. The insert holding device and the suture holding device may consist of a flat sheet of material.

In the document WO 2016/005118 A1, a device for tying a knot is described. The device comprises a thread having a functional end and a pull end. A main body is provided and the thread is laid around the outer surface of the main body in the form of a prepared, still open knot, such that as a result of pulling on the pull end, the thread slides along the lateral surface and forms a closed knot.

SUMMARY

An aspect relates to technologies for supporting a user in providing and tightening a knot, in particular to improve handling and safety in comparison to existing knotting aids.

For achieving the aspect, an article, a method for producing a knotting device for the article, a method for producing an article as well as a method for forming and tightening a knot.

According to an aspect, an article for supporting a user in providing and tightening a knot is provided. The article comprises a knotting device which comprises a base section, a thread storage section provided on the base section, and a knot support element. The knot support element comprises at least one flap of a flat material folded into a frustoconical shape. The frustoconical shape is hollow and open on a base end of the frustoconical shape and on a tip end of the frustoconical shape. The article further comprises a thread comprising a first end and a second end opposite the first end along the length of the thread. The first end of the thread is arranged in the thread storage section and the second end of the thread forms a plurality of windings of a non-tightened knot. At least one of the windings is arranged on and around an outer surface of the frustoconical shape of the knot support element, the knot support element thereby supporting and holding open the non-tightened knot.

According to another aspect, a method for producing a knotting device for the article is provided. In embodiments, the method comprises the steps of providing a base section, forming a thread storage section on the base section, the thread storage section configured to hold a length of a thread, and forming a knot support element. Forming the knot support element comprises folding at least one flap of a flat material into a hollow frustoconical shape open on a base end of the frustoconical shape and on a tip end of the frustoconical shape, the knot support element configured to support and hold open a non-tightened knot by supporting at least one winding of a plurality of windings of the thread forming the non-tightened knot such that the at least one winding of the plurality of windings rests on and around an outer surface of the frustoconical shape.

According to a further aspect, a method for producing an article is provided. In embodiments, the method for providing an article comprises the steps of providing a knotting device by performing the method as described herein, arranging a first end of a thread in the thread storage section, forming, in a second end of the thread, a plurality of windings of a non-tightened knot and arranging at least one winding of the plurality of windings on and around an outer surface of the frustoconical shape of the knot support element.

According to an additional aspect, a method for forming and tightening a knot is provided, the method comprising the steps of providing an article as described herein, passing the first end of the thread first through the open tip section of the frustoconical shape, then through the hollow frustoconical shape and then through the open base section of the frustoconical shape, sliding the at least one of the plurality of windings of the non-tightened knot off the tip end of the frustoconical shape and tightening the knot by pulling on the first end and on the second end of the thread. In embodiments, the method for forming and tightening a knot does not include any steps of treatment of the human or animal body by surgery or therapy, in particular no steps of surgical intervention on the human body. Thus, in embodiments, the method is non-surgical. There is also provided the article as described herein for use in surgery by passing the first end of the thread, which in this case is a surgical suture, first through the open tip section of the frustoconical shape, then through the hollow frustoconical shape and then through the open base section of the frustoconical shape, sliding the at least one of the plurality of windings of the non-tightened knot off the tip end of the frustoconical shape and tightening the knot by pulling on the first end and on the second end of the suture.

The frustoconical shape may be in the form of a frustum of a cone with any base shape of the base of the cone. In particular, the base shape may be a round shape, for example a circular shape or an elliptical shape. Alternatively, the base shape may have a different type of shape such as elliptical or polygonal, for example rectangular or trapezoid, optionally with rounded corners. In particular, the frustoconical shape may be a shape of a pyramid frustum, a pyramid being a specific type of cone, namely a cone with a polygonal base shape. With regard to all base shapes including round base shapes, the frustoconical shape may include crease lines, in particular resultant from folding the at least one flap into the frustoconical shape, resulting in the base shape exhibiting deviations from a nominal shape, for example corner-like deviations at end points of creases in a round base shape. With regard to ends of the frustoconical shape, the base end is the end of the frustoconical shape at which the base of the cone frustum is situated and the tip end of the frustoconical shape is the end opposite the base end along the cone frustum's height oriented towards the apex of the (imaginary) cone of which the frustoconical shape is a frustum. The tip end of the frustoconical shape may be closer to an edge of the knotting device, in particular closer to an edge of the base section, than the base end of the frustoconical shape.

The frustoconical shape may vary along the height of the cone frustum. For example, the frustoconical shape may be a shape consisting of more than one cone frustum stacked onto each other. This may result in a change in angle of the outer surface of the frustoconical shape along its height from the base end to the tip end. Alternatively or additionally, the frustoconical shape may be rounded along the height of the cone frustum, for example resulting in a bottle-like shape. Generally, the frustoconical shape of the knot support element tapers towards the tip end. In particular, the knot support element may vary in radius in order to avoid movement of windings of a suture resting thereon. The cross section and/or the tapering of the frustoconical shape may be provided such that radii of a plurality of windings of a suture resting thereon are increased at least to a value allowing to reduce or prevent kinks or other shapes (memory effects) impressed upon such suture by storage around the knot support element.

Within the meaning of the disclosure, a flat material is a material extending substantially less in one spatial dimension than in the other two spatial dimensions. In this sense, the flat material may be essentially two-dimensional. For example, the thickness of the flat material may be at least one order of magnitude smaller than both the length and the width. The flat material may comprise a paper material. Alternatively or additionally, the flat material may comprise a paper-like material, a plastic material, a metal material or a combination thereof. The flat material may be a sterilizable material.

Folding the at least one flap of the flat material into the hollow frustoconical shape may comprise rolling the flap into the frustoconical shape. Within the meaning of the present disclosure, a flap folded into a certain shape, in particular a frustoconical shape, may be a flap rolled into such shape.

With regard to arranging at least one winding of a plurality of windings on and around the outer surface of the frustoconical shape, exactly one winding of the plurality of windings, all windings of the plurality of windings or any desired number of the plurality of windings may be arranged on and around the outer surface of the frustoconical shape. In particular, the number of windings of a plurality of windings of a thread forming a non-tightened knot may be chosen to ensure safe storage of the non-tightened knot in the knotting device by the knot support element.

The knot support element may comprise two flaps of the flat material or of the further flat material folded into the frustoconical shape. In alternative embodiments, the knot support element may comprise more than two flaps. In embodiments in which the knot support element comprises more than one flap, the flaps may be folded and arranged with respect to each other to form the outer perimeter of the frustoconical shape with sections of the flaps providing sections of the outer perimeter while other sections of the flaps may not form part of the outer perimeter of the frustoconical shape, but may for example be arranged inside the frustoconical shape. The flaps may be folded from an outside of the frustoconical shape to an inside of the frustoconical shape, from an inside of the frustoconical shape to an outside of the frustoconical shape or different flaps may be folded in different directions.

The knot support element may comprise a slit which is provided in the frustoconical shape and is extending from the base end of the frustoconical shape to the tip end of the frustoconical shape. In embodiments, two flaps may form the slit by providing a distance between such flaps in sections of the flaps forming part of the outer perimeter of the frustoconical shape. In this case, the flaps may be folded inward with respect to the frustoconical shape forming edges of the slit, in particular rounded edges.

The base section may be formed from a cutout of the flat material or of a further flat material. The cutout may be cut out of the flat material or the further flat material using any known method, for example mechanical cutting, including punching and die cutting, laser cutting and/or waterjet cutting. Alternatively, the cutout may not be formed by cutting but may be any shape with the appearance of a shape that has been cut out. For example, the cutout may be formed by additive manufacturing, such as 3D printing, in particular already in its desired shape. By forming the knotting device using a cutout of a flat material, the volume of the knotting device may be minimized. Forming at least the base section of the knotting device from a cutout of a flat material may provide a knotting device that is dispensable and/or sterilizable. Further, manufacturing and logistics costs may be reduced by forming the knotting device using a cutout of a flat material.

In embodiments, while the knot support element comprises the at least one flap of the flat material folded into the frustoconical shape, the base section may be formed from a cutout of a further flat material. In such embodiments the flat material of the at least one flap is fixed to the cutout of the further flat material, for example by gluing, welding and/or stapling. In particular, the further flat material may be fixed to the base section. With regard to the further flat material, the embodiments described with regard to the flat material apply accordingly.

The cutout of the flat material may comprise the at least one flap of the knot support element. For example, the at least one flap may be a section of the cutout directly or indirectly attached to the base section. In another example, the at least one flap may be provided by a cut in the base section itself and the frustoconical shape may be formed by folding the at least one flap out of the base section.

In general, the knotting device may be formed out of a cutout provided as a single piece. For example, the cutout may be cut out of the flat material as a single shape without the need of assembling several pieces. The cutout may comprise sections that provide all parts of the support member when folded, for example in the form of flaps. By using a single-piece cutout, the knotting device may be manufactured from a single part or a small number of parts.

In alternative embodiments, the base section may not be formed of a cutout of a flat material. For example, the base section may be formed with a box or cartridge which may, for example, be formed using a casting method or additive manufacturing. In such embodiments, the flat material forming the at least one flap of the knot support element may be formed as a flat section of the same material as the base section or the flat material forming the at least one flap of the knot support element may be fixed to the base section, for example by gluing, welding and/or stapling.

At least one section of the base end of the frustoconical shape may be formed contiguous with the base section, such that moving one or more windings of the non-tightened knot arranged on and around the outer surface of the frustoconical shape off the base end is prevented. For example, a cutout of the flat material may comprise the at least one flap and the base end of the flap may be connected, directly or indirectly, to the base section in the cutout. The base section may be wider than the base end of the frustoconical shape at the base end, thereby preventing windings of the non-tightened knot arranged on and around the outer surface of the frustoconical shape from moving off the base end.

The knotting device may comprise a security flap formed adjacent to the knot support element, configured to be arranged on the tip end of the frustoconical shape such that moving one or more windings of the non-tightened knot arranged on and around the outer surface of the frustoconical shape off the tip end is prevented, and movable relative to the tip end of the frustoconical shape such that the security flap can be moved away from the tip end of the frustoconical shape such that moving one or more windings of a non-tightened knot arranged on and around the outer surface of the frustoconical shape off the tip end is possible. In an example, the security flap may be pivotably connected to the base section, for example by being formed contiguous with the base section and being pivotable by folding relative to the base section, and comprise a first security flap section configured to be arranged on the tip end of the frustoconical shape and a second security flap section arranged relative to the first security flap section on an opposite side of a pivoting point or line of the security flap such that pressing on the second security flap section pivots the first security flap section away from the tip end of the frustoconical shape, releasing windings of the non-tightened knot arranged on and around the outer surface of the frustoconical shape. In examples, the cutout of the flat material may comprise the security flap. In particular, the knotting device including the security flap may be formed out of a cutout provided as a single piece.

The security flap may be fixed in a position in which it is arranged on the tip end of the frustoconical shape by a retaining element. The retaining element may be a retaining tab or flap under which the security flap may be slipped and thereby held in place. The retaining tab or flap may be a small tab or flap such that the retaining tab or flap has a high stiffness to support holding the security flap in place. Alternatively, the retaining element may be a clip, an adhesive point, a magnet or a hook and loop fixation means.

The security flap may be configured to release the plurality of windings by applying a defined force. The defined force may be applied to the security flap itself, the knot support element and/or the thread forming a plurality of windings at least one of which is arranged on and around the frustoconical shape. The retaining element may be dimensioned such that the defined force leads to the release of the security flap from the retaining element.

The thread storage section may be arranged on the base section adjacent to a first end of the base section and the knot support element may be arranged on the base section adjacent to a second end of the base section opposite the first end, such that the knot support element comes to rest on the thread storage section when the base section is folded onto itself along a base folding line running between the thread storage section and the knot support element from a third end of the base section adjacent to the first and second ends and a fourth end of the base section opposite the third end and adjacent to the first and second ends. Herein, the base section, which in embodiments may be formed from a cutout, may comprise one half which encompasses the thread storage section and another half which encompasses the knot support element, and the first half may be folded onto the second half by folding the cutout in the middle. Such an arrangement may be provided in particular in embodiments in which a cutout of the flat material comprises the at least one flap of the knot support element. Thereby, the knotting device may provide both the knotting device for supporting a user in providing and tightening a knot as such and a packaging of the knotting device as such, by enclosing the thread storage section and the knot support element when the knotting device, in particular the cutout, is folded in half. Function of the knotting device as a packaging may include protections of elements arranged in the packaged knotting device, in particular a thread and more particularly windings of such thread forming a non-tightened knot and/or other windings of such thread such as windings provided for compact storage of the thread. In different embodiments, the knotting device, in particular a cutout from which the knotting device is formed, may comprise additional sections and/or flaps. In such embodiments a section encompassing the knot support element may still be folded onto a section encompassing the thread storage, thereby providing a packaging for the knotting device as such with the knotting device itself.

The base section may comprise a crease along the base folding line. The crease may be pre-formed for easing folding along the folding line or may be formed when the base section is first folded along the folding line.

In general, the thread may be a suture. In particular, the knotting device may be configured for use with a surgical suture. In this case, the thread storage section is configured to hold a length of a surgical suture and the knot support element supports and holds open a non-tightened knot by supporting a plurality of windings of the surgical suture. In such embodiments, the surgical suture may be any desired surgical suture, such as a monofilament suture, a multifilament suture, a braided suture, a suture made of a natural material and/or a suture made of a synthetic material.

The knotting device may comprise a surgical tool support element formed on or adjacent to the suture storage section. In alternative embodiments, the knotting device may comprise a surgical tool support element that is not formed on or adjacent to the suture storage section, for example a surgical tool support element that is formed adjacent to the knot support element. The surgical tool support element may be configured to secure a surgical tool to the knotting device. The article may comprise a surgical tool. In embodiments, in which the knotting device of the article comprises a surgical tool support element, the article may comprise a surgical tool secured to the surgical tool support element. In such embodiments, the suture may be a surgical suture. The surgical tool may be fixed to the suture, in particular, in the article, the surgical tool may be fixed to the first end of the suture.

The surgical tool may be any tool for performing a function in connection with a surgical suture during surgery. In particular, the surgical may be a surgical needle. Such surgical needle may be used for piercing tissue and guiding the surgical suture through such tissue to perform suturing at a surgical site. Alternatively, the surgical tool may be a fixation tool. For example, the surgical tool may be a surgical anchor or suture anchor. Such surgical anchor or suture anchor may be used for anchoring the surgical suture at a surgical site. For example, the surgical suture may be anchored by fixing the surgical anchor or suture anchor to bone. For example, the surgical anchor or suture anchor may be fixed by screwing the surgical anchor or suture anchor into a receiving structure, such as bone, at a surgical site.

The surgical tool support element may be made of a material which may be pierced with the surgical tool, for example a surgical needle to secure the needle in place, such as a soft material. For example, the surgical tool support element may be provided as a foam block, a wax block and/or a kneading compound. Alternatively, the surgical tool support element may be provided by the material of the knotting device itself, in particular by the cutout of the flat material. For example, the surgical tool support element may be an area of the cutout in which the paper material may be pierced by the surgical tool, for example a flap. Alternatively, the surgical tool support element may be provided as a magnet, a clip for clipping the surgical tool into, at least one press-on tab, a locking mechanism, such as a bayonet mount, tape or glue. The surgical tool support element may be adapted for repeatedly securing and releasing the surgical tool.

In embodiments, the knotting device may be formed out of a cutout provided as a single piece, including the surgical tool support element. For example, the surgical tool support element may be a flap of the cutout. In other embodiments, the knotting device may be formed out of a cutout provided as a single piece, as described herein, with exception of the surgical tool support element. In such embodiments the surgical tool support element, for example a foam block, may be fixed to the cutout before, after or during forming of the knotting device from the cutout.

The knotting device may comprise at least one storage flap provided in the suture storage section and configured to receive a length of a thread, for example a suture. In particular, the at least one storage flap may receive a plurality of windings of a thread not forming a knot for storing a length of the thread wound around the at least one storage flap. The first end of the thread may be wound around the at least one storage flap such that the thread is not biased towards a shape in which it is stored and the storage section, for example in a figure-8 shape or O-shape. The at least one storage flap may be movable from a first position, in which the first section of the thread may be wrapped around the at least one storage flap, to a second position, in which the at least one storage flap does not engage with the first section of the thread and the first section of the thread is freely removable from the storage section.

Alternatively, the at least one storage flap may be folded into an envelope-like structure for enclosing a length of thread. The first end of the thread may be arranged in the envelope-like structure, for example in windings not forming a knot. For forming an envelope-like structure, the at least one storage flap may be configured, in particular with regard to its size, to form one or more envelope sections of the cutout of the flat material.

The knotting device may comprise a plurality of storage flaps with at least one of the plurality of storage flaps receiving a plurality of windings of a thread not forming a knot for storing a length of the thread wound around the at least one of the plurality of storage flaps and at least one other of the plurality of storage flaps being folded into an envelope-like structure for enclosing a length of thread. The first end of the thread may be wound around the at least one of the plurality of storage flaps and may at the same time be arranged in the envelope-like structure provided by the at least one other of the plurality of storage flaps.

The cutout of the flat material or the further flat material may comprise the at least one storage flap. In particular, the knotting device may be formed out of a cutout provided as a single piece or may be formed out of a cutout provided as a single piece with the exception of a surgical tool support element.

The storage section may comprise holes configured to receive pins around which the thread may be wrapped. In particular, the pins may be placed in the holes for producing the article. The pins may be removed from the holes after the first section of the thread has been wrapped around the pins and the finished article may not comprise the pins. The first section of the thread may be wrapped around the pins such that the thread is not biased towards a shape in which it is stored in the storage section. For example, the first section of the thread may be wrapped around the pins in a figure-8 shape or an O-shape.

The first end and the second end of the thread may, respectively, have any length. In particular, the first end and the second end may be directly adjacent to each other and the thread may consist entirely of the first end and the second end. Alternatively, the thread may comprise a middle section between the first end and the second end.

The knot used may be any type of knot. The second end of the thread may be provided with a plurality of knots. For example, a plurality of knots may be provided with the plurality of windings, at least one of which is to be arranged on and around the frustoconical shape.

The article may comprise a sterile or sterilizable packaging enclosing the knotting device, the thread, in particular a surgical suture, and, in articles comprising a surgical tool, the surgical tool. The article may be a disposable or single-use article. Components of the article may be separately disposable. For example, the packaging may be disposed of after removing the knotting device, the thread and, in embodiments of the article comprising a surgical tool, the surgical tool from the packaging. The knotting device may be disposed of after the thread has been removed from the knotting device. Parts of the thread may be disposed of after a knot has been formed and tightened. In particular, the surgical tool and parts of the thread provided as a surgical suture may be disposed of after suturing is finished at a surgical site. Parts of the suture remaining at the surgical site may be removed and disposed of after sufficient healing or may remain at the surgical site.

The article may comprise, in a sterile or sterilizable packaging, more than one of each of the knotting device, the thread and optionally the surgical tool. For each combination of knotting device, thread and, if applicable, surgical tool, the embodiments described above may apply. Thereby, more than one knotting device combined with a thread and optionally a surgical tool may be provided in one sterile or sterilizable packaging. For example, five knotting devices, each with a corresponding thread and a corresponding surgical tool, may be provided in one sterile or sterilizable packaging.

The knotting device may comprise a pull end securing element for securing a pull end of a thread. In the article, the pull end of the thread may be an extreme end of the second section of the thread. The pull end may serve to tighten the knot after the at least one of the plurality of windings has been moved off the knot support element by pulling the pull end. The pull end securing element may be provided as a tab or flap, a clip, an adhesive point or a similar structure for securing the pull end. As an alternative, the pull end may run in a rail and access to the pull end may be provided by a recess in the outer side of the rail. For example, the rail may be formed by a rail flap of the knotting device under which the pull end is arranged longitudinally and the rail flap may be provided with an opening or recess, which may for example be provided as a hole cut into the rail flap, through which the pull end is accessible.

The knotting device may comprise interaction points which a user of the knotting device may interact with when using the knotting device. The knotting device may be provided with markings for usage indication. For example, the interaction points may be visually marked or provide haptic cues. Interaction points may, with regard to the knotting device and/or the article, include any or all of the surgical tool, the surgical tool support element, the security flap, the pull end securing element and a grip zone for holding the knotting device. The grip zone may have a surface with haptic or visual indications for better handling. The knotting device may further comprise alphanumerical lettering and/or symbols. For example, the alphanumerical lettering and/or the symbols may indicate a sequence of operating steps for using the knotting device and/or for using the article.

The knotting device may retain its desired shape after folding without the need for additional fixation means, such as glue or staples. For example, the cutout may be provided with additional tabs or flaps and respective slots such that, during folding, a respective tab or flap is inserted into a respective slot. Thereby, a section of the cutout may be fixed in its position and the knotting device may retain its desired shape.

In embodiments, the method for forming and tightening a knot may be used, for example, for model building. For example, in embodiments, the method may be used in building a so-called ship in a bottle by placing the article outside the bottle, inserting the first end of the thread into the bottle and passing it through a loop or similar structure of a ship model placed inside the bottle and passing the first end out of the bottle. The first end may then be passed through the frustoconical shape, the at least one of the plurality of windings may be slid off the frustoconical shape and the knot may be passed into the bottle and onto the ship model by pulling the first and second ends to tighten the knot.

The knot may be closed at a desired time by guiding the first end of the thread through the plurality of windings, guiding the at least one of the plurality of windings off the frustoconical shape and tightening the knot. The guiding of the first end through the plurality of windings may take place before or after the guiding of the at least one winding off the frustoconical shape (at least in part). Alternatively or additionally, the guiding of the first end through the plurality of windings may take place during the guiding of the at least one winding off the frustoconical shape, at least in part. For example, a first part of the first end may be guided through the plurality of windings and a second part of the first end may not yet be guided through the plurality of windings. The at least one winding may then be guided off the frustoconical shape and over the first end, thereby guiding the second part of the first end through the plurality of windings. In embodiments comprising a surgical tool, the embodiments outlined above with regard to passing the first end through the plurality of windings may apply to passing the surgical tool through the plurality of windings, accordingly.

According to the disclosure, a cutout for forming the knotting device is provided. The cutout is made from a flat material. In particular, the cutout may be a shape cut out of the flat material. The cutout may be cut out of the flat material using any known method, for example mechanical cutting, including punching and die cutting, laser cutting and/or waterjet cutting. Alternatively, the cutout may not be formed by cutting but may be any shape with the appearance of a shape that has been cut out. For example, the cutout may be formed by additive manufacturing, such as 3D printing, in particular already in its desired shape. The cutout may be provided as a sterile cutout. The cutout may be manufactured as a single piece. For example, the cutout may be cut out of the flat material as a single shape without the need of assembling several pieces. The cutout may comprise sections that provide all parts of the knotting device when folded. By providing the cutout as a single piece, the knotting device may be manufactured from a single part or a small number of parts.

The cutout is configured to be folded into the knotting device described herein. To this end, the cutout comprises different sections that may be folded relative to each other. The sections may comprise sections arranged adjacent and separate from yet connected to each other as part of the cutout. Alternatively or additionally the sections may comprise a first section and a second section arranged within the first section and separated from the first section by a cut not forming a closed curve such that the second section is connected to the first section and foldable relative thereto. Further sections arranged within other sections may be provided accordingly.

With the article and the method for forming and tightening a knot, faster and easier execution of knotting may be provided in comparison to hand-tying a knot, for example, with regard to the article, in minimally invasive surgery. In particular, in comparison to hand-tying a surgical knot, which is the standard of care, and depending on the expertise of the surgeon performing the knotting, a reliable knot execution and consequently relative higher patient safety may be enabled in comparison to average surgical hand-knotting. In comparison to known surgical suturing devices, cost and/or complexity of use may be reduced. Consequently, a wider range application may be provided in comparison to known devices.

Embodiments described above with reference to the knotting device may apply accordingly to the article, the method for producing a knotting device, the method for producing an article and/or the method for forming and tightening a knot and vice versa.

BRIEF DESCRIPTION

Some of the embodiments will be described in detail, with references to the following Figures, wherein like designations denote like members, wherein:

FIG. 4A shows a schematic depiction of steps of producing an article comprising a knotting device, a suture and a surgical tool;

FIG. 4B shows a schematic depiction of steps of producing an article comprising a knotting device, a suture and a surgical tool;

FIG. 5B shows a schematic depiction of steps of producing an article comprising a knotting device, a suture and a surgical tool;

FIG. 5C shows a schematic depiction of steps of producing an article comprising a knotting device, a suture and a surgical tool;

FIG. 5D shows a schematic depiction of steps of producing an article comprising a knotting device, a suture and a surgical tool.

DETAILED DESCRIPTION

Figure 1:
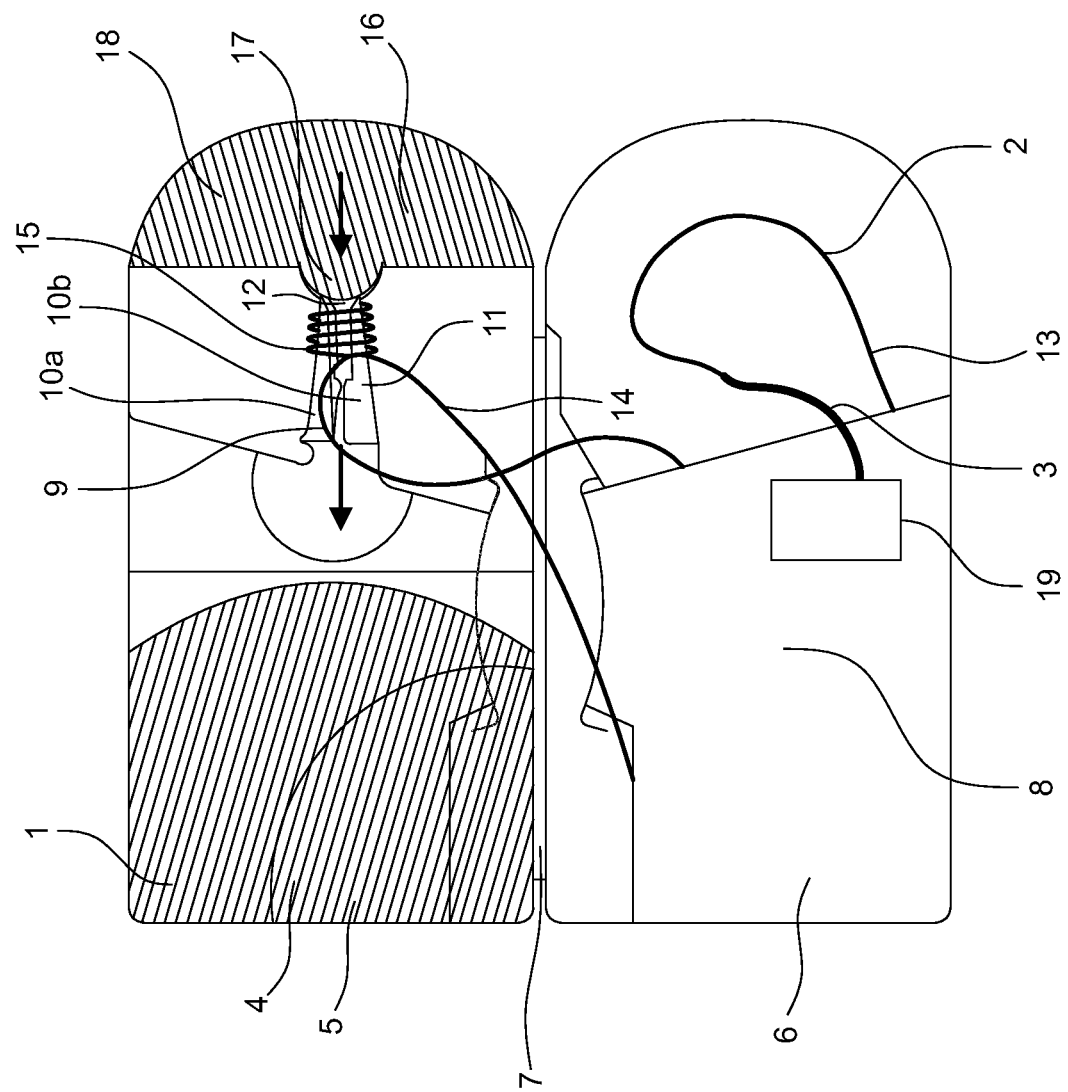
FIG. 1 shows a schematic view of an article with a knotting device, a suture and a surgical tool.

FIG. 1 shows a schematic view of an article comprising a knotting device 1, a thread 2, which in the embodiment shown is a surgical suture, and a surgical tool in the form of a surgical needle 3. The knotting device 1 is folded from a cutout of a flat material. A base section 4 of the knotting device 1 has two parts which in the depiction of FIG. 1 form a top section 5 and a bottom section 6. The top section 5 and the bottom section 6 may be folded onto each other along a base folding line 7 to close the knotting device 1.

On the bottom section 6 of the base section 4, thread storage section, which in the embodiment shown is a suture storage section 8, is provided. In the embodiment of FIG. 1, the suture storage section 8 comprises an envelope-like structure which, as may be seen in FIG. 1, is configured to hold a length of the suture 2.

On the top section 5 of the base section 4, a knot support element 9 is arranged. The knot support element 9 comprises two flaps 10a, 10b folded or rolled up into a frustoconical shape 11. The flaps 10a, 10b are formed out of the cutout and connected thereto at a base end of the frustoconical shape 11. The base shape of the frustoconical shape 11 approximates a circle. However, due to the connection to the rest of the cutout and the nature of the process of folding or rolling, the circle is deformed with a flattened section at the point of connection with the rest of the cutout and kinks along its circumference where the frustoconical shape 11 has creases caused by folding or rolling. Further, the cross-sectional shape of the frustoconical shape 11 varies along its height. The frustoconical shape has a slit 12 formed by a distance between edges of the flaps 10a, 10b. As can be seen in FIG. 1, the width of the slit 12 varies along the height of the frustoconical shape 11 due to the shape of the flaps 10a, 10b.

The needle 3 is connected to an extreme end of a first end 13 of the suture 2. The first end 13 of the suture 2 is stored in the suture storage section 8. In particular, most of the first end 13 of the suture 2 is arranged in the envelope-like structure of the suture storage section 8.

A second end 14 of the suture 2 forms an open, non-tightened knot by being arranged in a plurality of windings 15. The plurality of windings 15 are placed on the outer surface of the frustoconical shape 11. Thereby, the plurality of windings 15 are held open by the frustoconical shape 11. Further, the elasticity of the flaps 10a, 10b leads to a force expanding the frustoconical shape 11, thereby keeping the plurality of windings 15 under tension. An extreme end of the second end 14 of the suture 2 is led back to the storage section 8 and stored in the envelope-like structure of the storage section 8.

The plurality of windings 15 are kept form sliding off the base end of the frustoconical shape 11 both by the widening of the frustoconical shape 11 towards the base end and by the much wider configuration of the rest of the cutout to which the flaps 10a, 10b are connected at the base end of the frustoconical shape 11. The plurality of windings 15 are kept from sliding off the tip end of the frustoconical shape 11 by a security flap 16. The security flap 16 is integral with the rest of the cutout and connected thereto along a fold line. A smaller securing section 17 of the security flap 16 is placed on the tip end of the frustoconical shape 11, thereby keeping the tip end in place and preventing the plurality of windings 15 from sliding off the tip end. A larger actuating section 18 of the security flap 16 is arranged opposite the fold line from the securing section 17. Due to such placement, exerting a pressure on the actuating section 18 in the direction into the drawing plane of FIG. 1 causes the security flap 16 to pivot around the fold line, lifting the securing section 17 off the tip end of the frustoconical shape and thereby releasing the tip end. With the tip end released, the plurality of windings 15 can slide off the tip end of the frustoconical shape 11.

The needle 3 is held in place by a surgical tool support element 19 which, in the example of FIG. 1, is a piece of adhesive tape placed on the needle 3 and the knotting device 1 fixing the needle 3 to the knotting device 1.

Figure 2:
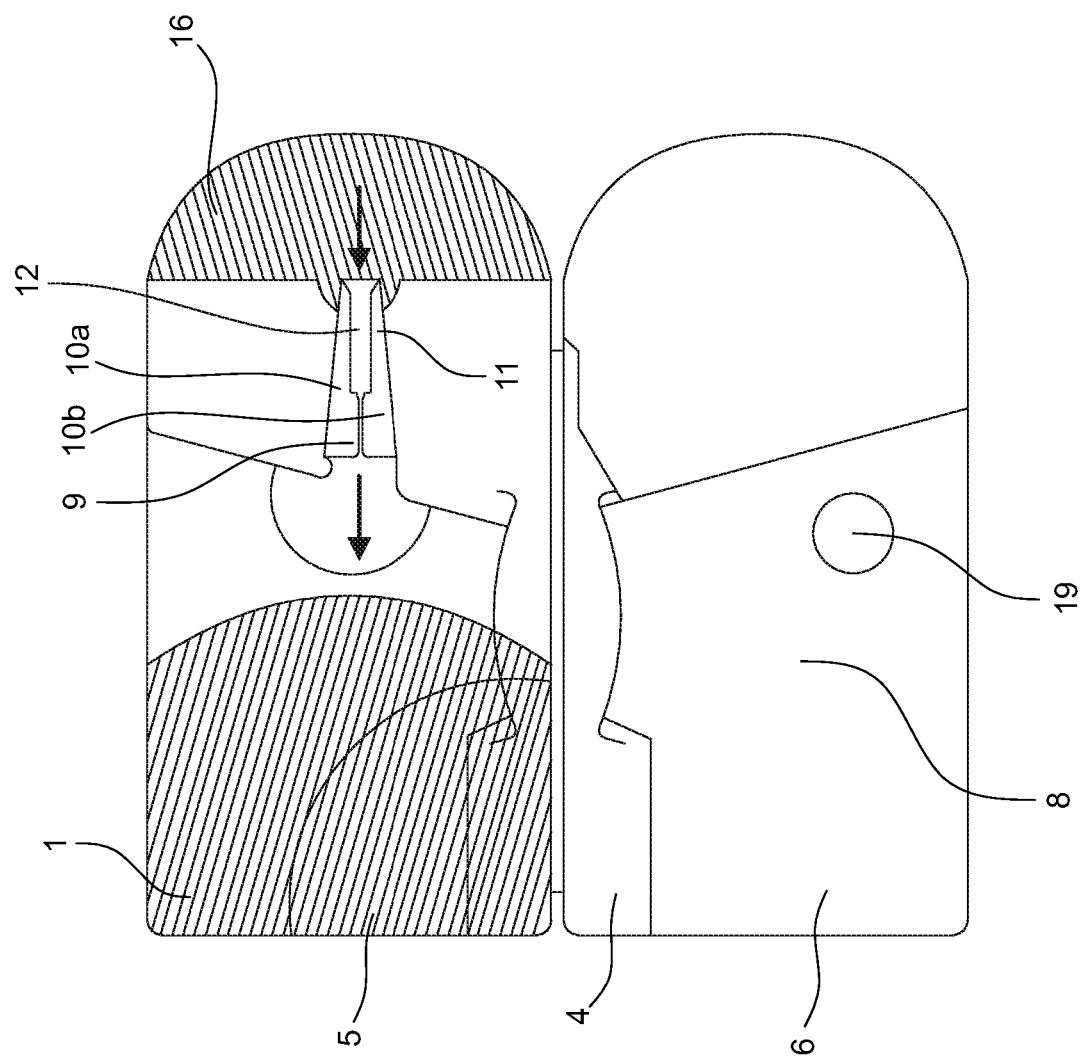
FIG. 2 shows a schematic view of a knotting device with a surgical tool support element.

FIG. 2 shows a schematic view of a knotting device 1. In comparison to the knotting device 1 of FIG. 1, the surgical tool support element 19 of the knotting device 1 of FIG. 2 is a foam block glued to the cutout of the knotting device 1. A surgical tool, in particular a needle 3, may pierce the foam block, thereby fixing the surgical tool to the knotting device 1.

Figure 3:
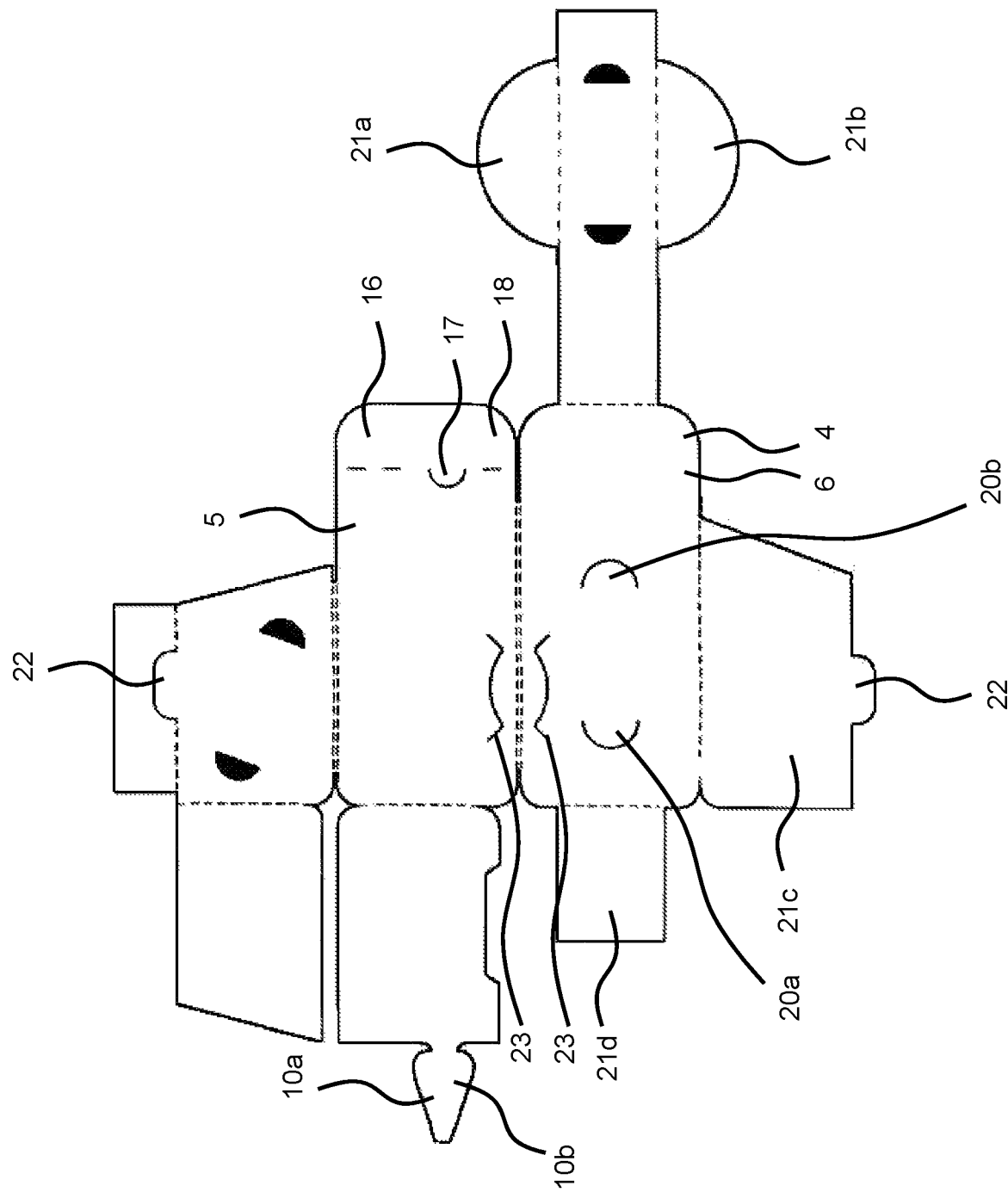
FIG. 3 shows a cutout for forming a knotting device.

FIG. 3 shows a cutout for forming a knotting device 1. In the example shown, the cutout is cut from a sheet of a flat material using punching and allows forming a complete knotting device 1 with the exception of a surgical tool support element 19 which may be attached to the knotting device 1 once it has been folded from the cutout.

The cutout comprises a base section 4 with a top section 5 and a bottom section 6. The top section 5 comprises a flap forming a subsection (on the left side in FIG. 3) to which flaps 10a, 10b are connected from which the frustoconical shape 11 of a knot support element 9 is to be folded or rolled. The top section further comprises a security flap 16 with a securing section 17 and an actuating section 18 which may be pivoted by folding along a demarcated fold line of the top section 5. The bottom section 6 comprises elements which are to be folded into a suture storage section 8. Two storage flaps 20a, 20b may be folded up for winding a suture 2 around such storage flaps 20a, 20b. Further storage flaps 21a, 21b, 21c, 21d are adapted to be folded into an envelope-like structure for storing the suture 2 wrapped around the storage flaps 20a, 20b; the folding motion depicted by arrows in FIG. 4B.

For fixing the top section 5 and the bottom section 6 in a folded position after the knotting device 1 has been formed from the cutout, tabs 22 and corresponding slits 23 are provided. The tabs 22 may each be inserted into a corresponding slit 23 to secure a flap provided with the tab 22 in position.

FIGS. 4A to 4D illustrate producing an article comprising a knotting device 1, a thread provided as a surgical suture 2 and a surgical tool which is a needle 3 in the example shown.

According to FIG. 4A, a knotting device 1 is provided. A frustoconical shape 11 formed from flaps 10a, 10b of a knot support element 9 is provided on a top section 5 of a cutout from which the knotting device 1 is formed. The tip end of the frustoconical shape 11 is free. A thread or suture storage section 8 provided on a bottom section 6 is completely unfolded.

As shown in FIG. 4B, for producing an article, a plurality of windings 15 is formed in second end 14 of a suture. The plurality of windings 15 is placed on the outer surface of the frustoconical shape 11. Following, the tip end of the frustoconical shape 11 is placed under a securing section 17 of a security flap 18 (as shown in FIG. 4C). Thereby, the tip end of the frustoconical shape 11 is fixed in place and the plurality of windings 15 are prevented from sliding off the tip end of the frustoconical shape 11. In alternative embodiments, only one or any number of windings of the plurality of windings 15 may be placed on the outer surface of the frustoconical shape 11, as long as safe storage of a non-tightened knot provided by the plurality of windings 15 is ensured.

Storage flaps 20a, 20b of the suture storage section 8 are folded up and a first end 13 of the suture 2 is wound around the storage flaps 20a, 20b in a figure-8 shape. Following, storage flaps 21a, 21b and 21d are folded onto the wound first end 13 of the suture 2, forming an envelope-like structure enclosing the first end of the suture 13 (as shown in FIG. 4C).

FIG. 4C shows a step of closing the suture storage section 8 by folding a storage flap 21c over the envelope-like structure; the folding motion depicted by an arrow. At the same time, a needle 3 attached to the extreme end of the first end 13 of the suture 2 is moved out of the suture storage section 8 along with part of the first end 13 of the suture 2. The storage flap 21c is fixed in the folded-over position by inserting a tab 22 into a corresponding slit 23. It is to be noted that a flap of the top section 5 has accordingly been fixed in place by inserting tabs 22 into corresponding slits 23 as can be seen on the left side of FIG. 4C.

Figure 4D:
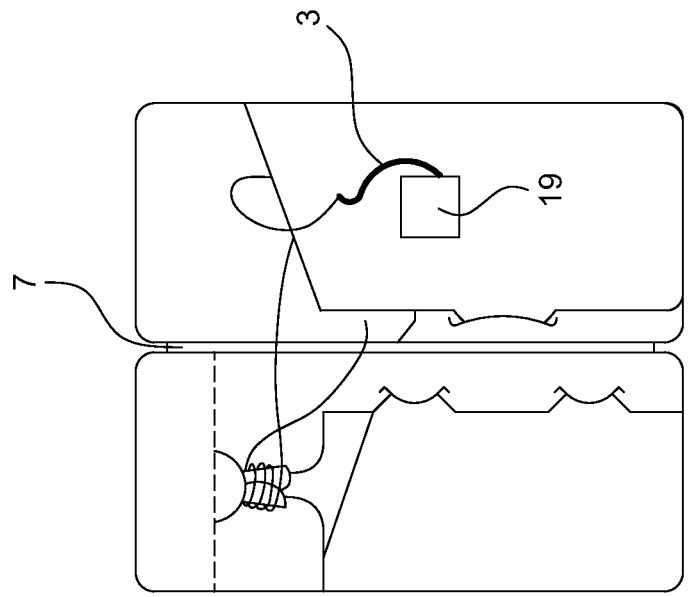
FIG. 4D shows a schematic depiction of steps of producing an article comprising a knotting device, a suture and a surgical tool.
Figure 4C:
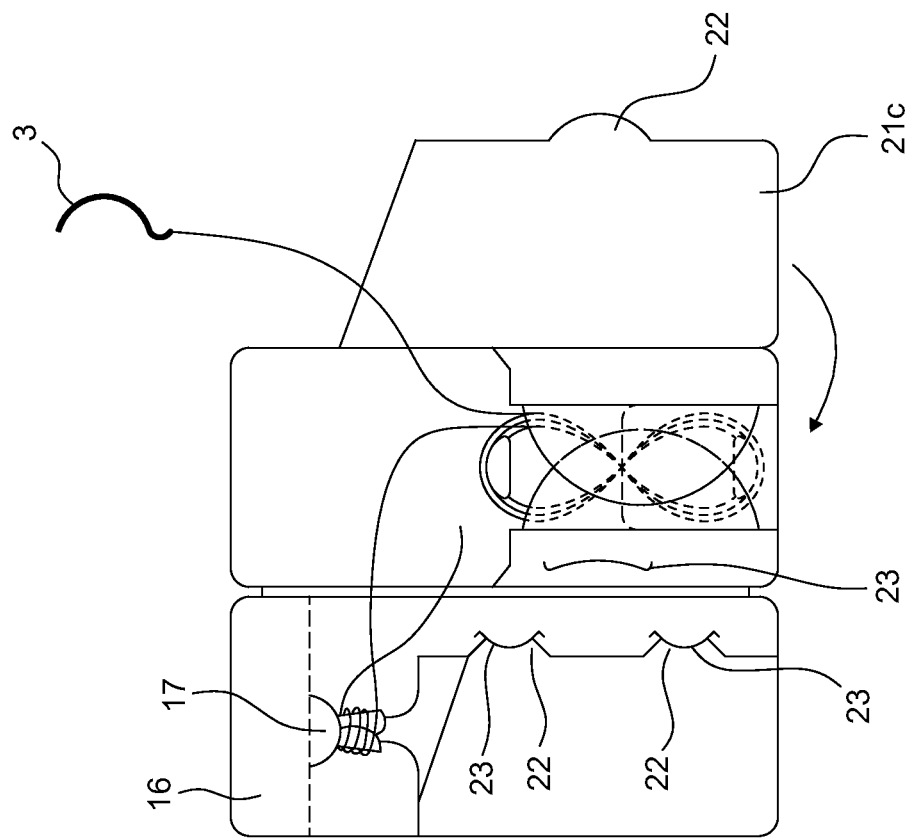
FIG. 4C shows a schematic depiction of steps of producing an article comprising a knotting device, a suture and a surgical tool.

Finally, as shown in FIG. 4D, the needle is fixed to a surgical tool support element 19 provided with a foam block by piercing the foam block with the needle 3. For packaging the article, the knotting device 1 may be folded in half along a base fold line 7, arranging the top section 5 on the bottom section 6 and thereby the knot support element 9 on the suture storage section 8. The knotting device 1 may thus provide at least part of the packaging of the article, improving handling of the article and protecting the needle while allowing suture delivery from a sterilizable and discardable material from which the knotting device 1 is formed.

FIGS. 5A to 5E show a use of an article comprising a knotting device 1, a thread 2 and a surgical tool which is a needle 3 in the example shown. The use shown in FIGS. 5A to 5E is with regard to placing a knot at a surgical site. However, the article may be used in different scenarios, for example model building, in which a thread, which may be any desired thread, has to be knotted at a site that is hard to reach or/and at which there is little space for forming, placing and tightening the knot.

Figure 5A:
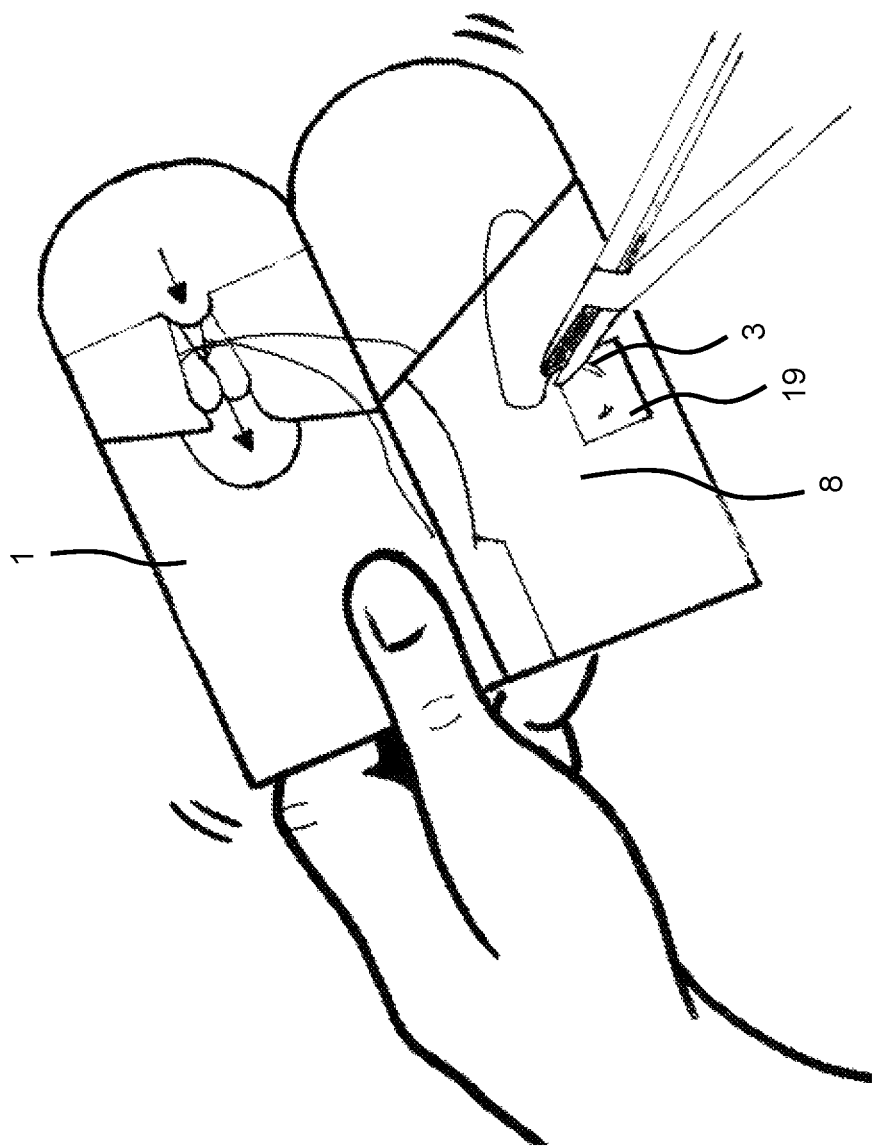
FIG. 5A shows a schematic depiction of a use of an article comprising a knotting device, a suture and a surgical tool.

As shown in FIG. 5A, the knotting device 1 is opened and the needle 3 is grasped, in the example shown using a surgical needle holder, and removed from a surgical tool support element 19 on the knotting device 1. The needle 3 is then pulled away from the knotting device 1, thereby pulling and removing a first end 13 of a suture 2, to which the needle 3 is attached and which was placed in a suture storage section 8 of the knotting device 1, from the suture storage section 8, as shown in FIG. 5B. The needle and the first end 13 of the suture 2 are then free to use. In particular, stitches may be placed at a surgical site using the needle 3, for example closing a cut using the first end 13 of the suture 2.

After the needle 3 and the first end 13 of the suture have been used and a knot is to be places, as illustrated in FIG. 5C, the needle 3 is inserted into an open tip end of a frustoconical shape 11 of a knot support element 9 of the knotting device. The needle 3 is guided through the hollow frustoconical shape 11 and out of an open base end of the frustoconical shape 11. Thereby, the needle is also guided through a plurality of windings 15 or loops of a knot formed in a second end 14 of the suture 2, placed on and held open by the outer surface of the frustoconical shape 11. The needle 3 is then pulled away from the knot support element 9, pulling the first end 13 of the suture 2 along. Thereby, the first end 13 of the suture 2 is guided through the plurality of windings 15 of the knot, as well.

After first guiding the needle 3 through the frustoconical shape 11 and before pulling the needle 3 away from the knot support element 9, it is usually necessary to change the grip on the needle 3. For changing the grip, flaps 10a, 10b of the knot support element 9 forming the frustoconical shape 11 may also serve to hold the needle 3 in place while the grip is released. To achieve this, pressure may be exerted on the frustoconical shape 11, in particular on the flaps 10a, 10b while the needle 3 is at least partially placed inside the frustoconical shape. The needle 3 is thus fixated and a user may momentarily let go of needle 3 to change their grip of the needle 3.

In FIG. 5D, it can be seen that the plurality of windings 15 of the knot may be released from the knot support element 9 by pushing on an actuation section 18 of a security flap 16. Pushing on the actuation section 18 causes the security flap 16 to pivot around a fold line, thereby moving a securing section 17 of the security flap 16, which was previously placed on a tip end of the frustoconical shape 11, fixing the tip end in place, away from the tip end of the frustoconical shape 11. The tip end is thereby released and the plurality of windings 15 of the knot are free to slide off the frustoconical shape 11.

Figure 5E:
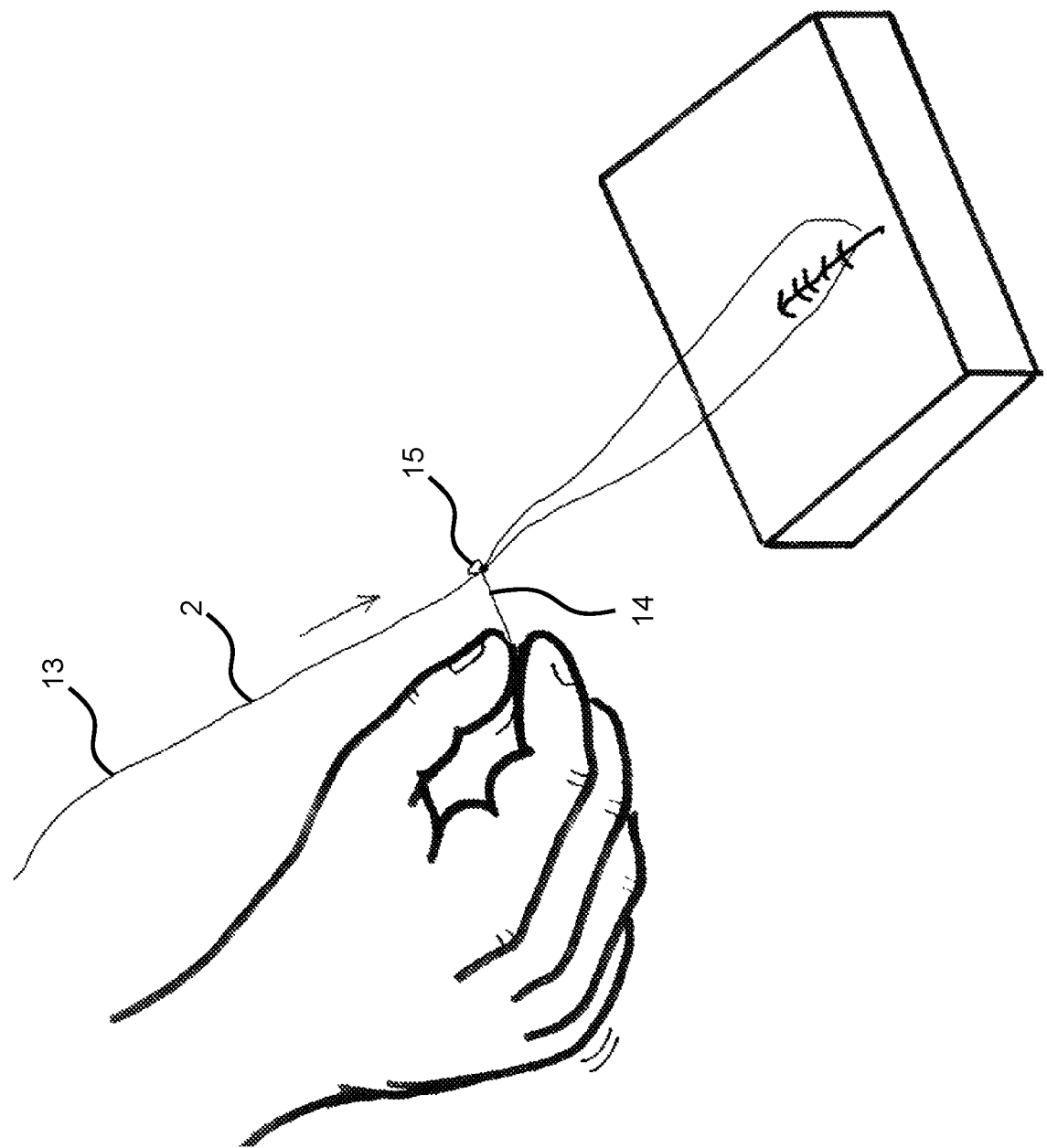
FIG. 5E shows a schematic depiction of steps of producing an article comprising a knotting device, a suture and a surgical tool.

FIG. 5E illustrates tightening the knot. To tighten the knot, the plurality of windings 15 are slid along the length of the suture 2 towards the desired location of the knot. There, the knot is tightened by pulling on both the first end 13 and the second end 14 of the suture 2. The suture 2 may then be trimmed at the knot and the knotting device 1, the needle 3 and the trimmed sections of the suture 2 may be discarded.

As outlined above, the article according to the disclosure may be used in non-surgical contexts. In particular, the article may be used in any context in which it is desirable to form a knot in a thread 2 at a distance from the site of final placement of the knot by forming the knot at the knotting device 1 as outlined above and then moving it to the site of final placement along the thread 2.

Although the invention has been illustrated and described in greater detail with reference to the exemplary embodiment, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

The claims are as follows:

1. An article for supporting a user in providing and tightening a knot, comprising:
   a knotting device having:
      a base section;
      a thread storage section provided on the base section; and
      a knot support element comprising at least one flap of a flat material folded into a frustoconical shape, the frustoconical shape being hollow and open on a base end of the frustoconical shape and on a tip end of the frustoconical shape; and
   a thread having a first end and a second end opposite the first end along the length of the thread,
   wherein
      the first end of the thread is arranged in the thread storage section; and
      the second end of the thread forms a plurality of windings of a non-tightened knot, at least one of which is arranged on and around an outer surface of the frustoconical shape of the knot support element, the knot support element thereby supporting and holding open the non-tightened knot.

2. The article according to claim 1, wherein the knot support element includes two flaps of the flat material folded into the frustoconical shape.

3. The article according to claim 1, wherein the knot support element comprises a slit provided in the frustoconical shape and extending from the base end of the frustoconical shape to the tip end of the frustoconical shape.

4. The article according to claim 1, wherein the base section is formed from a cutout of the flat material or of a further flat material.

5. The article according to claim 4, wherein the cutout comprises the at least one flap of the knot support element.

6. The article according to claim 1, wherein at least one section of the base end of the frustoconical shape is formed contiguous with the base section, such that moving one or more windings of a non-tightened knot arranged on and around the outer surface of the frustoconical shape off the base end is prevented.

7. The article according to claim 1, wherein the knotting device comprises a security flap, the security flap
   formed adjacent to the knot support element;
   configured to be arranged on the tip end of the frustoconical shape such that moving one or more windings of a non-tightened knot arranged on and around the outer surface of the frustoconical shape off the tip end is prevented; and
   movable relative to the tip end of the frustoconical shape such that the security flap can be moved away from the tip end of the frustoconical shape such that moving one or more windings of a non-tightened knot arranged on and around the outer surface of the frustoconical shape off the tip end is possible.

8. The article according to claim 1, wherein the thread storage section is arranged on the base section adjacent to a first end of the base section and the knot support element is arranged on the base section adjacent to a second end of the base section opposite the first end, such that the knot support element comes to rest on the thread storage section when the base section is folded onto itself along a base folding line running between the thread storage section and the knot support element from a third end of the base section adjacent to the first and second ends and a fourth end of the base section opposite the third end and adjacent to the first and second ends.

9. The article according to claim 8, wherein the base section comprises a crease along the base folding line.

10. The article according to claim 1, wherein the knotting device includes a surgical tool support element formed on or adjacent to the thread storage section.

11. The article according to claim 1, wherein the knotting device includes at least one storage flap provided in the thread storage section and configured to receive a length of a thread.

12. The article according to claim 4, wherein the cutout of the flat material comprises the at least one storage flap.

13. A method for producing a knotting device for the article of claim 1, comprising:
providing a base section;
forming a thread storage section on the base section, the thread storage section configured to hold a length of a thread; and
forming a knot support element, comprising folding at least one flap of a flat material into a hollow frustoconical shape open on a base end of the frustoconical shape and on a tip end of the frustoconical shape, the knot support element configured to support and hold open a non-tightened knot by supporting at least one winding of a plurality of windings of the thread forming the non-tightened knot such that the at least one winding of the plurality of windings rests on and around an outer surface of the frustoconical shape.

14. A method for producing an article, comprising:
providing a knotting device by performing the method of claim 13;
arranging a first end of a thread in the thread storage section;
forming, in a second end of the thread, a plurality of windings of a non-tightened knot; and
arranging at least one winding of the plurality of windings on and around an outer surface of the frustoconical shape of the knot support element.

15. A method for forming and tightening a knot, comprising:
providing the article according to claim 1;
passing the first end of the thread first through the open tip section of the frustoconical shape, then through the hollow frustoconical shape and then through the open base section of the frustoconical shape;
sliding the at least one winding of the plurality of windings of the non-tightened knot off the tip end of the frustoconical shape; and
tightening the knot by pulling on the first end and on the second end of the thread.

* * * * *